United States Patent [19]

Herbst et al.

[11] Patent Number: 5,482,597
[45] Date of Patent: Jan. 9, 1996

[54] PURIFICATION OF CRUDE (METH)ACRYLIC ACID

[75] Inventors: Holger Herbst, Frankenthal; Gerhard Nestler, Ludwigshafen, both of Germany; Jerry Darlington, Lake Jackson, Tex.; Hans Martan, Frankenthal, Germany

[73] Assignee: BASF Aktiengesellschaft, Ludwigshafen, Germany

[21] Appl. No.: 347,131

[22] Filed: Nov. 23, 1994

[51] Int. Cl.$^6$ .............................. B01D 3/34; C07C 51/44
[52] U.S. Cl. ..................... 203/38; 203/DIG. 21; 203/59; 562/600
[58] Field of Search .................... 203/38, 29, 34, 203/DIG. 21, 59; 562/600

[56] References Cited

U.S. PATENT DOCUMENTS

| | | |
|---|---|---|
| 3,725,208 | 4/1973 | Maezawa et al. ............... 203/DIG. 21 |
| 3,893,895 | 7/1975 | Dehnert et al. ................. 203/DIG. 21 |
| 4,828,652 | 5/1989 | Schropp ......................... 203/DIG. 21 |
| 5,196,578 | 3/1993 | Kuragano et al. ...................... 562/600 |

FOREIGN PATENT DOCUMENTS

| | | | |
|---|---|---|---|
| 48-31087 | 9/1973 | Japan | ..................... 562/600 |
| 49-95920 | 9/1974 | Japan | ..................... 562/600 |
| 52-23017 | 2/1977 | Japan | ..................... 562/600 |
| 61-218556 | 9/1986 | Japan | ..................... 562/600 |

*Primary Examiner*—Wilbur Bascomb, Jr.
*Attorney, Agent, or Firm*—Oblon, Spivak, McClelland, Maier & Neustadt

[57] ABSTRACT

In a process for purifying crude (meth)acrylic acid, the crude (meth)acrylic acid is worked up by distillation after addition of an organic carboxylic acid hydrazide and, if desired, an organic sulfonic acid.

16 Claims, No Drawings

PURIFICATION OF CRUDE (METH)ACRYLIC ACID

The present invention relates to a process for removing aldehydes from crude (meth)acrylic acid which has been produced by the catalytic gas-phase oxidation process, in which the crude (meth)acrylic acid is admixed with a hydrazine derivative and the (meth)acrylic acid is distilled from the mixture.

(Meth)acrylic acid is used as an abbreviation and denotes acrylic acid or methacrylic acid.

(Meth)acrylic acid, either as such or in the form of its esters, is particularly important for preparing polymers for a very wide range of applications, e.g. use as adhesives.

(Meth)acrylic acid can be obtained, inter alia, by catalytic gas-phase oxidation of alkanes, alkanols, alkenes or alkenals containing 3 or 4 carbon atoms. It can be particularly advantageously obtained, for example, by catalytic gas-phase oxidation of propene, acrolein, tert-butanol, isobutene, iso-butane, iso-butyraldehyde or methacrolein. However, other possible starting compounds are those from which the actual $C_4$ starting compound is only formed as an intermediate during the gas-phase oxidation. An example which may be mentioned is the methyl ether of tert-butanol. These starting gases, generally diluted with inert gases such as nitrogen, $CO_2$, saturated hydrocarbons and/or steam, are passed in admixture with oxygen at elevated temperatures and, if desired, superatmospheric pressure over transition metal mixed oxide catalysts, oxidized to (meth)acrylic acid and separated from the product gas stream by absorption in a suitable absorbant (e.g. water or a mixture of from 70 to 75% by weight of diphenyl ether and from 25 to 30% by weight of biphenyl) (cf., for example, EP-A 297 445 and DE-C 21 36 396).

After removal of the absorbant (and, if desired, prior desorption by stripping, e.g. using air, of contaminants having a low solubility in the absorbant) by extractive and/or distillative separation processes (e.g. removal of the absorbant water by distillation, azeotropic distillation or extractive separation of the acid from the aqueous solution and subsequent distillative removal of the extractant), there is obtained an acid which is here described as crude (meth)acrylic acid.

Owing to numerous parallel and secondary reactions occurring in the course of the catalytic gas-phase oxidation, the crude (meth)acrylic acid does not form a pure product. Rather, it contains a spectrum of various contaminants (in general of the order of ≦2% by weight, cf. EP-B 169 254) comprising mostly aldehydes related to the starting compounds of the catalytic gas-phase oxidation and to the resulting (meth)acrylic acid. Crude (meth)acrylic acid therefore generally contains formaldehyde, acetaldehyde, acrolein, methacrolein, propionaldehyde, n-butyraldehyde, benzaldehyde, furfural and crotonaldehyde, as well as acetic, formic and propionic acid as contaminants.

For various applications of (meth)acrylic acid, the contaminants contained in the crude (meth)acrylic acid have a disadvantageous effect (cf., for example, DE-B 22 07 184). Thus, for example, the induction time of polymerization reactions, i.e. the time between reaching the polymerization temperature and the actual commencement of polymerization, may not be reproducible or the degree of polymerization may be reduced. The polymers can also tend to become discolored.

Efforts are therefore made, for such applications, to largely remove the contaminants from the crude (meth)acrylic acid and to convert crude (meth)acrylic acid into pure (meth)acrylic acid. This is generally carried out by distillation, e.g. by two successive rectification stages to remove contaminants boiling at a higher or lower temperature than the (meth)acrylic acid (cf., for example, EP-B 102 642).

However, a problem is that at least a part of the aldehydic contaminants is so similar in its physical behavior to the (meth)acrylic acid that a removal of the same by rectification alone is only possible using an uneconomical number of separation plates and/or an uneconomical reflux ratio.

GB-B 1 346 737 and DE-B 22 07 184 accordingly disclose a process for purifying crude acrylic acid wherein compounds containing an $-NH_2$ group are added to the crude acrylic acid and the acrylic acid is distilled from the mixture. The primary amines bind the contaminating aldehydes to a great extent, so that even a subsequent simple distillation step achieves a high degree of separation in respect of the aldehydic contaminants. The smallest residual amounts of aldehydes are achieved using hydrazine and phenylhydrazine as amine compounds. However, a disadvantage of the use of the latter compounds is that hydrazine and phenylhydrazine are not toxicologically acceptable. EP-A 270 999 therefore recommends admixing crude (meth)acrylic acid, prior to the distillative workup, with guanylhydrazine (aminoguanidine) and/or salts thereof (preferably aminoguanidine hydrogen carbonate) in amounts of from 1 to 3 mol per mole of aldehyde present. However, a disadvantage of aminoguanidine and/or salts thereof is that the rate of their reaction with aldehydes may not be completely satisfactory. DE-A 43 35 172 recommends additionally adding an organic sulfonic acid prior to the distillative workup to avoid deposit formation. JP-A 117 716/75 recommends, in the absence of amine compounds, the combination phenothiazine/sulfonic acid to reduce the polymerization tendency of acrylic acid.

It is an object of the present invention to provide a process for removing aldehydes from crude (meth)acrylic acid which has been produced by the catalytic gas-phase oxidation process, in which the crude (meth)acrylic acid is admixed with a hydrazine derivative which does not have the disadvantages of the abovementioned hydrazine compounds of the prior art and the (meth)acrylic acid is distilled from the mixture.

We have found that this object is achieved by a process for removing aldehydes from crude (meth)acrylic acid which has been produced by the catalytic gas-phase oxidation process, in which the crude (meth)acrylic acid is admixed with a hydrazine derivative and the (meth)acrylic acid is distilled from the mixture, wherein the hydrazine derivative used is the hydrazide of an organic carboxylic acid.

Examples of such hydrazides of organic carboxylic acids are, in particular, semicarbazide (carbamic acid hydrazide) and the monohydrazides and dihydrazides of saturated aliphatic monocarboxylic and/or dicarboxylic acids having from 1 to 10 carbon atoms. These are, in particular, the hydrazides of formic acid, acetic acid, propionic acid, butanoic acid and pentanoic acid. Suitable saturated aliphatic dicarboxylic acids for the corresponding hydrazides are, in particular, those which have from 4 to 8 carbon atoms. The dihydrazide of adipic acid and succinic acid are particularly suitable. Of course, it is also possible to use salts of the carboxylic acid hydrazides in place of the hydrazides themselves. Suitable salts are, for example, the hydrogen carbonate, nitrate, sulfate or chloride, e.g. semicarbazide hydrochloride.

The aldehyde content, which has to be known to determine the absolute amount of carboxylic acid hydrazide to be added, can be determined in a manner known to those skilled in the art by high-pressure liquid chromatography (HPLC) after converting the aldehydes into suitable derivatives. Generally, at least 0.5 mol, but usually not more than 5 mol, of carboxylic acid hydrazide compound is added per mole of aldehydic contaminants. The amount of carboxylic acid hydrazide to be added is, on the same basis, preferably from 1 to 3 mol and particularly preferably from 1 to 2 mol.

Preferably, the addition of the carboxylic acid hydrazide of the invention is carried out only shortly before the distillative workup. In other words, the carboxylic acid hydrazide of the invention is added to the crude (meth)acrylic acid, the mixture is left for some time (the reaction time depends on the temperature; at from 20° to 100° C., it is from a few minutes to a number of hours, in practice it is advantageous to leave the mixture to stand at room temperature) and is then worked up by distillation. The carboxylic acid hydrazides of the invention can be added either as such or in solution (suitable solvents are, for example, water or (meth)acrylic acid).

The process of the invention is frequently impaired to a certain extent by the distillation apparatus (in particular the vaporizer surface) becoming relatively rapidly coated during the distillative separation with a deposit which is caused by the presence of the carboxylic acid hydrazides of the invention and/or salts thereof, since it does not occur in a distillative workup of the crude (meth)acrylic acid in the absence of these additives (although such an additive-free distillative workup results in only a low degree of separation of the aldehydic contaminants in the crude (meth)acrylic acid).

Obviously, direct reaction products of the carboxylic acid hydrazides and/or their salts with the aldehydic contaminants and/or secondary products formed from these during the distillative workup are involved in the deposit formation.

It is accordingly also an object of the present invention to provide a process for removing aldehydes from crude (meth)acrylic acid which has been produced by the catalytic gas-phase oxidation process, in which the deposit formation described is reduced.

We have found that this object is achieved by a process for removing aldehydes from crude (meth)acrylic acid which has been produced by the catalytic gas-phase oxidation process, in which the crude (meth)acrylic acid is admixed with carboxylic acid hydrazide of the invention and/or salts thereof and the (meth)acrylic acid is distilled from the mixture, wherein the crude (meth)acrylic acid has added to it, prior to the distillative treatment, at least one organic sulfonic acid and/or salts thereof (in particular the alkali metal salts) in addition to the carboxylic acid hydrazide and/or salts thereof added. It is advantageous if the organic sulfonic acid is such that on addition to water at 25° C. it reduces the surface tension of the latter. In general, at least 0.1 mol, but usually not more than 5 mol, of at least one organic sulfonic acid is added per mole of carboxylic acid hydrazide compound added, since above this amount no improved action is achieved. Preferably, from 0.5 to 2 mol of at least one organic sulfonic acid are added per mole of carboxylic acid hydrazide compound added. The addition of the organic sulfonic acid can be either before, simultaneously with or after the addition of the carboxylic acid hydrazide compound, as desired. Furthermore, the addition of the organic sulfonic acid can be made only on the trays of the distillation column, at the top of the column or via the reflux to the column. The addition of the organic sulfonic acid is successful even if deposit formation has already occurred.

Suitable organic sulfonic acids are, for example, alkylsulfonic acids of the general formula $R^1$—SO$_3$H, where $R^1$ is $C_1$- to $C_{20}$-alkyl. The salts of these alkylsulfonic acids are also suitable, in particular the alkali metal salts. A preferred representative is methanesulfonic acid and salts thereof.

Also suitable are arylsulfonic acids and salts thereof. Suitable arylsulfonic acid compounds are toluenesulfonic acids such as p-toluenesulfonic acid, benzenesulfonic acid, phenolsulfonic acids, xylenesulfonic acids, dibutylnaphthalenesulfonic acids and salts thereof, in particular alkali metal salts thereof. Particularly suitable, however, are alkylarylsulfonic acids and salts thereof, among which preference is in turn given to those which have only one alkyl substituent. Aryl is preferably a benzene or naphthalene ring system.

The alkyl radical advantageously has from 5 to 16 carbon atoms.

Particularly suitable are the alkylbenzenesulfonic acids and salts thereof, i.e. compounds of the general formula

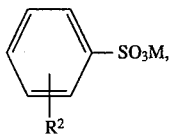

where M is hydrogen or another cation, e.g. an alkali metal ion, and $R^2$ is $C_5$- to $C_{16}$-alkyl.

$R^2$ is preferably $C_8$- to $C_{12}$-alkyl.

Among the alkylbenzenesulfonic acid compounds of the above general formula, the dodecylbenzenesulfonic acids and their salts are in turn of particular importance. This applies particularly to dodecylbenzenesulfonic acid compounds of the general formula

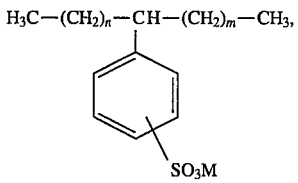

where n, m are integers whose sum must be 9. Quite generally, the arylsulfonic acid compound is preferably added in its fully acid form, i.e. the arylsulfonic acid is the preferred additive. This applies likewise to the alkylsulfonic acid compounds and to aralkylsulfonic acid compounds which are likewise suitable as organic sulfonic acid compound to be added according to the invention.

Of course, the process of the invention can also be used for removing aldehydes from (meth)acrylic acid which is not crude (meth)acrylic acid, i.e. which have been obtained in a way other than by gas-phase catalytic oxidation of $C_3$–$C_4$ compounds and thus is contaminated by aldehydic impurities for other reasons.

The distillative workup of the crude (meth)acrylic acid modified according to the invention is preferably carried out under reduced pressure, advantageously ≦100 mbar, generally from 10 to 100 mbar. Correspondingly, the associated boiling temperature is usually in the range from 70° to 105° C.

The process of the invention is of particular importance in the case of crude methacrylic acid whose preparation by catalytic gas-phase oxidation starts with methacrolein, in particular when the methacrolein is produced by catalytic gas-phase oxidation of tert-butanol, iso-butane or iso-butene or by reaction of formaldehyde with propionaldehyde as described in EP-B 92 097 or EP-B 58 927, and this particularly when the catalytic gas-phase oxidation of the tert-butanol, iso-butane or iso-butene is carried out using a catalytically active composition of the general formula I $$Mo_{12}Bi_aFe_bX^1_cX^2_dX^3_eX^4_gO_n \qquad (I),$$

where the variables have the following meanings:
$X^1$ nickel and/or cobalt,
$X^2$ thallium, an alkali metal and/or an alkaline earth metal,
$X^3$ phoshorus, arsenic, boron, antimony, tin, cerium, lead, niobium and/or tungsten,
$X^4$ silicon, aluminum, titanium and/or zirconium,
a from 0.5 to 5.0
b from 0.01 to 3.0
c from 3.0 to 10.0
d from 0.02 to 2.0
e from 0 to 5.0
g from 0 to 10 and
n a number which is determined by the valence and amount of the elements other than oxygen in I,
at temperatures of from 300° to 400° C. and, apart from the specific temperature-time profile, otherwise under the conditions described in DE-A 40 23 239 and the methacrolein obtained is used for further oxidation without intermediate purification. Furthermore, the process of the invention is particularly suitable when the catalytic gas-phase oxidation of the methacrolein, apart from the specific temperature-time profile, is carried out as described in DE-A 41 32 263 at temperatures of from 200° to 350° C. or as described in DE-A 41 32 648 at temperatures of from 250° to 400° C.

Of course, the process of the invention proceeds in the presence of polymerization inhibitors such as air, hydroquinone, hydroquinone monoethyl ether, paranitrosophenol, paramethoxyphenol or phenothiazine.

They are usually used in amounts of from 50 to 1000 ppm, based on the crude (meth)acrylic acid.

The process of the invention has been found to be particularly advantageous in the presence of phenothiazine and/or aromatic hydroxy compounds such as hydroquinone and hydroquinone monomethyl ether as polymerization inhibitors.

The process of the invention gives, on the one hand, particularly effective distillative removal of aldehydic contaminants from crude (meth)-acrylic acid and, on the other hand, largely suppresses the associated deposit formation. The process of the invention is therefore, for example, not only suitable for batchwise operation, but in particular for continuous operation as is described in DE-A 42 01 697.

EXAMPLES

Example 1

A crude acrylic acid containing a total amount of 420 ppm (based on the crude acrylic acid) of 2-furfural, 3-furfural and benzaldehyde was admixed at 25° C. with 1100 ppm of aminoguanidine hydrogen carbonate and subsequently left to stand while being maintained at 25° C. The content of the abovementioned aldehydes was determined as a function of time by means of gas chromatography. The results obtained are:

| Time (min) | Total amount of aldehyde (ppm, based on crude acrylic acid) |
| --- | --- |
| 5 | 380 |
| 30 | 250 |
| 60 | 80 |

Example 2

As Example 1, but the aminoguanidine hydrogen carbonate was replaced by an amount of adipic acid dihydrazide equimolar to the 1100 ppm of the former. Results obtained were:

| Time (min) | Total amount of aldehyde (ppm, based on crude acrylic acid) |
| --- | --- |
| 5 | 300 |
| 30 | 100 |
| 60 | 10 |

Example 3

As Example 1, but the aminoguanidine hydrogen carbonate was replaced by an amount of succinic acid dihydrazide equimolar to the 1100 ppm of the former. Results obtained were:

| Time (min) | Total amount of aldehyde (ppm, based on crude acrylic acid) |
| --- | --- |
| 5 | 20 |
| 30 | 10 |
| 60 | 10 |

Example 4

In a glass rectification column for continuous operation, whose vaporizer was a glass convection-circulation vaporizer which was heated by means of a metallic, electrically heatable reboiler, 140 ml/h of a crude acrylic acid were continuously fed in via the vaporizer, the crude acrylic acid having been obtained by catalytic gas-phase oxidation of acrolein as described in Example B1 of DE-A 43 02 991 and subsequent workup of the reaction gases as described in Example B1 of DE-A 21 36 396. The same amount of crude acid was continuously taken from the vaporizer. The vaporized crude acid was condensed above the rectification column and quantitatively returned as reflux to the top of the column. The column was stabilized by means of phenothiazine fed in at the top of the column. Before being fed to the vaporizer, the crude acrylic acid had been admixed with 1400 ppm of its weight of adipic acid dihyrazide. During the rectification, a deposit formed on the heating reboiler, the amount of the deposit equilibrating after an operating time of 8 hours. The result is shown in the following table. The table also shows the result which was obtained when the crude acrylic acid was admixed directly before being fed into the vaporizer with 1.5 mol of dodecylbenzenesulfonic acid per mole of adipic acid dihydrazide present (after 40 hours).

TABLE

| no addition of sulfonic acid | 2400 mg of deposit after 8 hours |
|---|---|
| with dodecylbenzene-sulfonic acid | <10 mg of deposit after 40 hours |

We claim:

1. A process for purifying an aldehyde-contaminated (meth)acrylic acid with a hydrazine derivative, which comprises distilling the (meth)acrylic acid from the mixture, wherein the hydrazine derivative used is a dihydrazide of a saturated aliphatic dicarboxylic acid having from 4 to 8 carbon atoms or the salt thereof or both.

2. The process as claimed in claim 1, wherein the dihydrazide of the saturated aliphatic dicarboxylic acid having from 4 to 8 carbon atoms is the dihydrazide of adipic acid or succinic acid.

3. The process as claimed in claim 1, wherein from 0.5 to 5 mol of the saturated aliphatic dicarboxylic acid dihydrazide compound is used per mole of aldehydic contamination.

4. The process as claimed in claim 2, wherein from 0.5 to 5 mole of the dihydrazide of adipic acid or succinic acid is used per mole of aldehydic contamination.

5. The process as claimed in claim 1, wherein the aldehyde-contaminated (meth)acrylic acid is a crude (meth)acrylic acid which has been produced by catalytic gas phase oxidation.

6. The process as claimed in claim 2, wherein the aldehyde-contaminated (meth)acrylic acid is a crude (meth)acrylic acid which has been produced by catalytic gas-phase oxidation.

7. The process as claimed in claim 1, which is effected continuously.

8. A process for purifying an aldehyde-contaminated (meth)acrylic acid, which comprises admixing the (meth)acrylic acid with a hydrazine derivative and distilling the (meth)acrylic acid from the mixture, wherein the hydrazine derivative used is a carboxylic acid hydrazide or the salt thereof or both and wherein the aldehyde-contaminated (meth)acrylic acid has added to it, prior to said distillation at least one organic sulfonic acid or a salt thereof or both in addition to the added carboxylic acid hydrazide or salts thereof or both.

9. The process as claimed in claim 8, wherein the hydrazine derivative used is the hydrazide of a saturated aliphatic monocarboxylic or dicarboxylic acid having from 1 to 10 carbon atoms or both.

10. The process as claimed in claim 8, wherein the carboxylic acid hydrazide used is a dihydrazide of a saturated aliphatic dicarboxylic acid having from 4 to 8 carbon atoms or the salt thereof or both 11. The process as claimed in claim 8, wherein the carboxylic acid hydrazide used is the dihydrazide of adipic acid or succinic acid.

12. The process as claimed in claim 8, wherein from 0.5 to 5 mol of organic carboxylic acid hydrazide compound is used per mole of aldehyde contamination.

13. The process as claimed in claim 8, wherein the aldehyde-contaminated (meth)acrylic acid is a crude (meth)acrylic acid which has been produced by catalytic gas phase oxidation.

14. The process as claimed in claim 8, wherein up to 5 mol of at least one organic sulfonic acid or a salt thereof or both is added per mole of carboxylic acid hydrazide compound added.

15. The process as claimed in claim 8, wherein from 1 to 3 mol of carboxylic acid hydrazide or salts thereof of both are added per mol of aldehydic contaminants, and from 0.5 to 2 mol of at least one organic sulfonic acid or a salt thereof or both are added per mole of carboxylic acid hydrazide compound added.

16. The process as claimed in claim 8, wherein the sulfonic acid compound added comprises dodecylbenzenesulfonic acid.

* * * * *